United States Patent
Iwata

(10) Patent No.: US 8,212,223 B2
(45) Date of Patent: Jul. 3, 2012

(54) PARTICLE BEAM IRRADIATION APPARATUS

(75) Inventor: Takaaki Iwata, Tokyo (JP)

(73) Assignee: Mitsubishi Electric Corporation, Chiyoda-Ku, Tokyo (JP)

(*) Notice: Subject to any disclaimer, the term of this patent is extended or adjusted under 35 U.S.C. 154(b) by 78 days.

(21) Appl. No.: 12/991,231

(22) PCT Filed: Jun. 9, 2009

(86) PCT No.: PCT/JP2009/060531
§ 371 (c)(1),
(2), (4) Date: Nov. 5, 2010

(87) PCT Pub. No.: WO2010/143267
PCT Pub. Date: Dec. 16, 2010

(65) Prior Publication Data
US 2011/0163243 A1    Jul. 7, 2011

(51) Int. Cl.
*G21K 5/04*    (2006.01)
(52) U.S. Cl. .................... 250/396 R; 250/492.3
(58) Field of Classification Search ............... 250/396 R, 250/396 ML, 492.3
See application file for complete search history.

(56) References Cited

U.S. PATENT DOCUMENTS

| 6,034,377 | A | 3/2000 | Pu |
| 7,560,715 | B2 | 7/2009 | Pedroni |
| 2008/0006776 | A1 | 1/2008 | Furukawa et al. |
| 2009/0039256 | A1 | 2/2009 | Fujii et al. |
| 2011/0121195 | A1* | 5/2011 | Harada et al. ........... 250/396 ML |
| 2011/0147604 | A1* | 6/2011 | Iwata ..................... 250/396 ML |

FOREIGN PATENT DOCUMENTS

| JP | 11-142600 | 5/1999 |
| JP | 2002-141199 A | 5/2002 |
| JP | 2005-296162 A | 10/2005 |
| JP | 2006-166947 A | 6/2006 |
| JP | 2007-132902 A | 5/2007 |
| JP | 2007-534391 A | 11/2007 |
| JP | 2009-000347 | 1/2009 |
| WO | WO 01/69643 A1 | 9/2001 |
| WO | WO 2005/102453 A1 | 11/2005 |
| WO | WO 2007/029520 A1 | 3/2007 |

OTHER PUBLICATIONS

Kanai et al., "Spot scanning system for proton radiotherapy", Med. Phys., Jul./Aug. 1980, pp. 365-369, vol. 7, No. 4. Ogawa et al., "Absorption Equivalent Thickness (AET) Method and Pencil Beam Method for Electron Beam Treatment Planning", Japanese J. Radiol. Technol., Sep. 9, 1986, pp. 628-634, vol. 42, No. 5 (English Summary included).
T. Iwata, U.S. Appl. No. 12/989,767, entitle "Particle Bean Irradiation Apparatus" filed on Oct. 26, 2010.

* cited by examiner

*Primary Examiner* — Kiet T Nguyen
(74) *Attorney, Agent, or Firm* — Buchanan Ingersoll & Rooney PC

(57) ABSTRACT

There is obtained a particle beam irradiation apparatus which does not use any IF sentence (conditional expression for case classification) and can calculate a control command and enhance irradiation position precision. The particle beam irradiation apparatus is provided with inverse mapping means having an inverse mapping mathematical expression model for generating an command value for the scanning electromagnet from a desired irradiation position coordinate of the charged particle beam in an irradiation subject so that irradiation to the irradiation subject is implemented on the basis of the command value concerned, and the scanning electromagnet is controlled on the basis of the command value generated from the desired irradiation position coordinate of the charged particle beam in the irradiation subject by using the inverse mapping mathematical expression model, thereby irradiating the irradiation subject with the charged particle beam while scanning the charged particle beam.

8 Claims, 13 Drawing Sheets

FIG.3
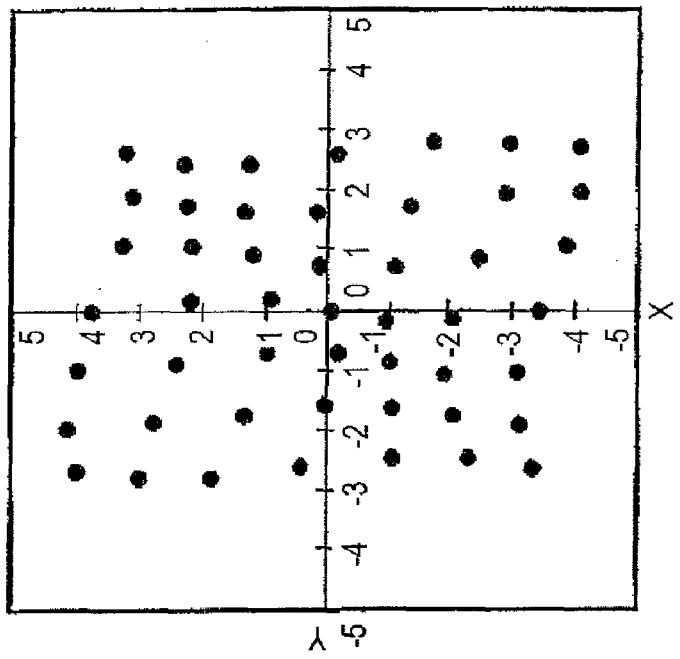
FORWARD MAPPING
(PHYSICAL PHENOMENON)
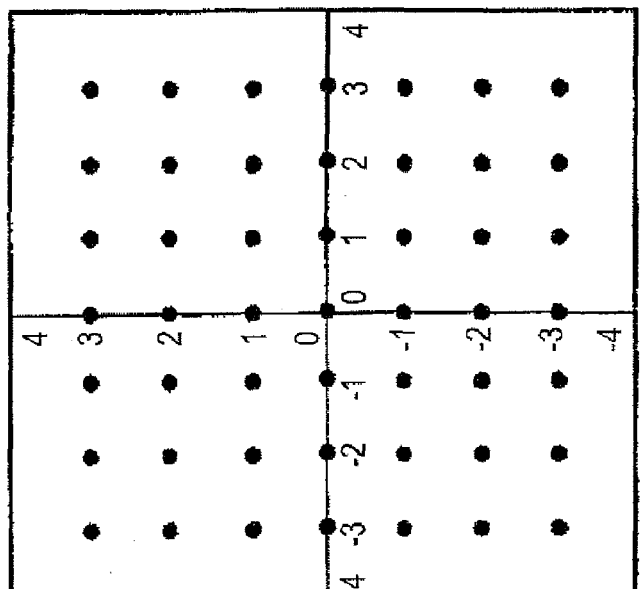

3a: X-DIRECTION SCANNING ELECTROMAGNET
3b: Y-DIRECTION SCANNING ELECTROMAGNET
12: FIRST BEAM PROFILE MONITOR
13: SECOND BEAM PROFILE MONITOR
14: WATER PHANTOM

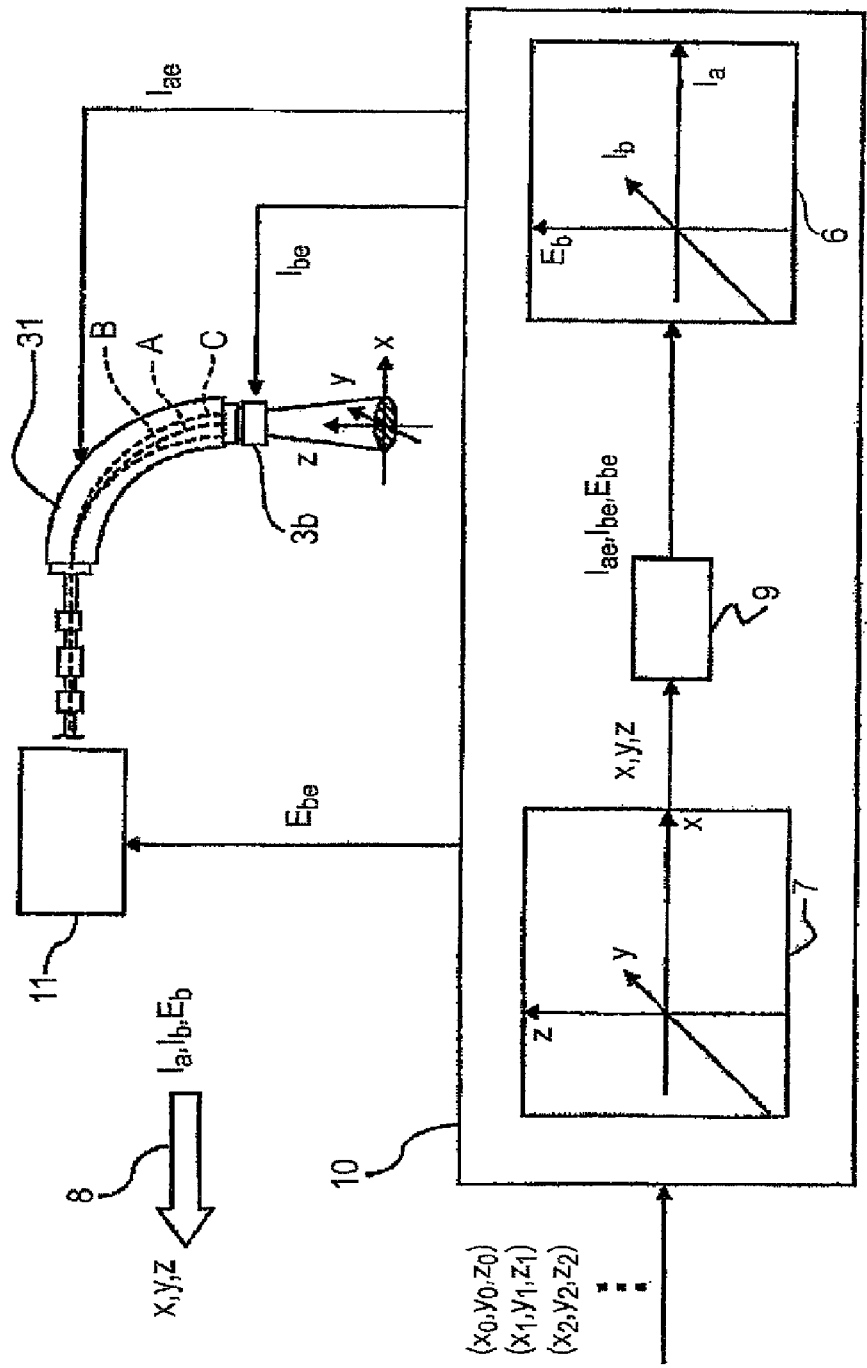

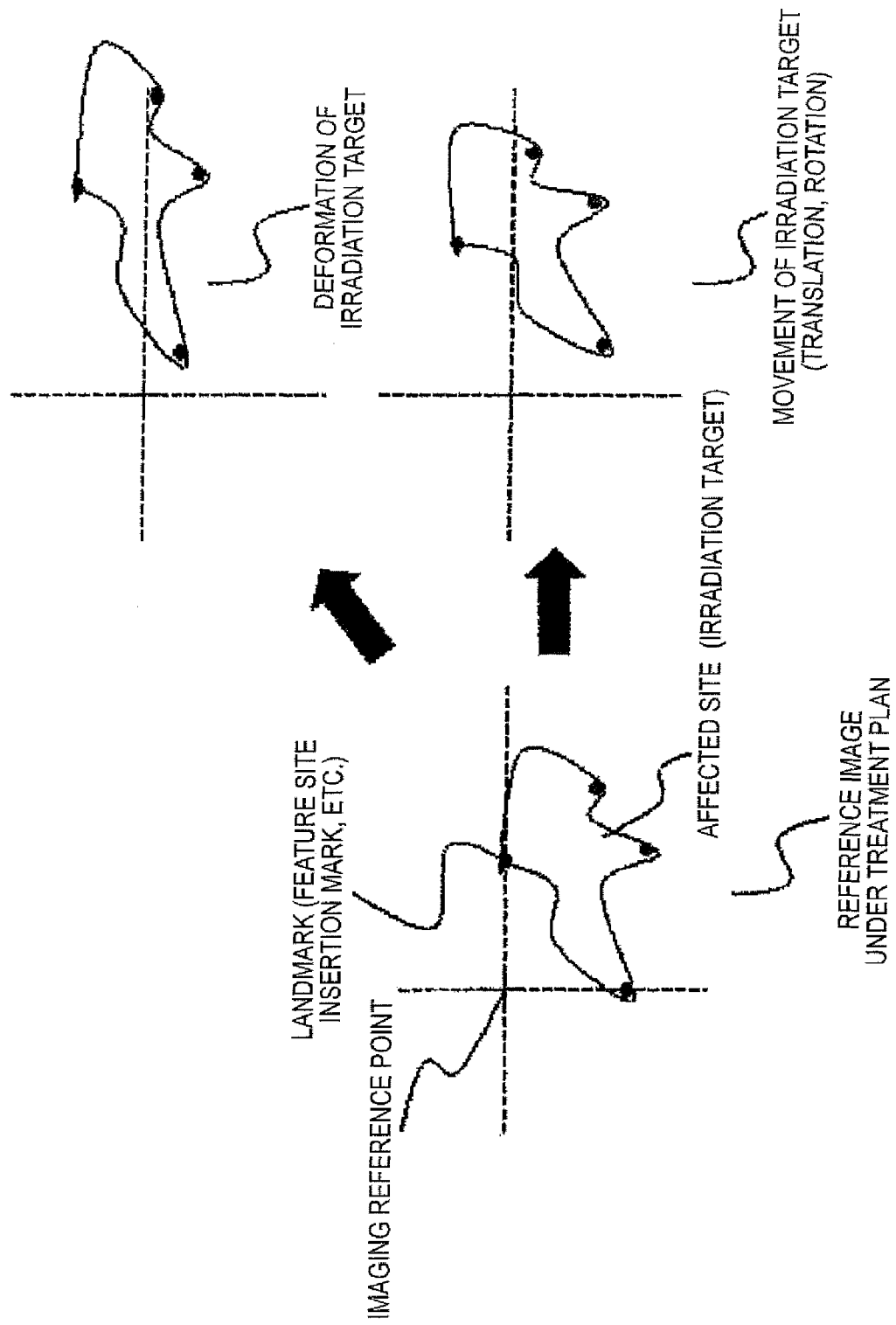

PARTICLE BEAM IRRADIATION APPARATUS

TECHNICAL FIELD

The present invention relates to a particle beam irradiation apparatus used for medical care such as a cancer treatment, etc. and for researches, and particularly to a particle beam irradiation apparatus for performing scanning irradiation such as spot-scanning, raster-scanning or the like.

BACKGROUND ART

According to a conventional particle beam irradiation apparatus for performing scanning irradiation, as disclosed in Patent Document 1, set current for a scanning electromagnet as scanning means is varied with time lapse to scan a charged particle beam. The value of the set current of the scanning electromagnet can be calculated according to a theoretical formula based on a specification of the scanning electromagnet, a specification of a power source for the scanning electromagnet and a specification of an irradiation beam (irradiation energy, incident beam position, etc.). However, the set current value for the scanning electromagnet calculated according to the theoretical formula is a theoretical value based on the premise that the specification of the scanning electromagnet, the specification of the scanning power source and the specification of the irradiation beam are never changed. Actually, the set current value is changed due to various factors, so that the irradiation position may be displaced and thus erroneous irradiation may occur.

For example, the scanning electromagnet is generally a bipolar electromagnet. Therefore, the beam irradiation position is potentially displaced from an estimated position due to residual magnetic field caused by hysteresis of the electromagnet although no current is supplied to the electromagnet. Furthermore, the beam irradiation position is also potentially displaced due to some secular variation of equipment although beams are irradiated under the same condition. Therefore, there has been proposed a method in which plural appropriate irradiation conditions (irradiation energy, etc.) are set to perform test irradiation under a state that no patient exists before a medical treatment is conducted or the like, a conversion table representing the relation of beam position data $(x_a, y_a)$ detected on a beam position monitor and set current values $(I_a, I_b)$ of the scanning electromagnet are stored in a storage device in advance and then a set current value of the scanning electromagnet is calculated by using the conversion table when irradiation for a treatment is performed (Patent Document 1).

PRIOR ART DOCUMENT

Patent Document

Patent Document 1: JP-A-2005-296162

SUMMARY OF THE INVENTION

Problem to be Solved by the Invention

According to the conventional scanning particle beam irradiation apparatus, the set current value (two-dimension) of the scanning electromagnet is calculated by using the conversion table as described above. Therefore, when the conversion table is referred to on the basis of desired irradiation position coordinates (two-dimension) of treatment irradiation, IF sentences (conditional expressions for case classification) must be frequently used or the program itself is required to be changed in accordance with variation of the size of the conversion table when the number of irradiation places for test irradiation is required to be increased or the like. Furthermore, when the control input of the particle beam irradiation apparatus is expanded to three dimension (two dimension for the set current values of the scanning electromagnet and one dimension for the set energy of the charged particle beam), there is a problem that the method using the conversion table is further complicated and thus it is difficult to implement this method. Particularly, when the position, posture and shape of an irradiation subject (diseased site) fluctuate from moment to moment due to breathing or the like, it is difficult to generate command values on a real-time basis according to the conventional method based on the conversion table.

The present invention has been implemented to solve the foregoing problem, and has an object to provide a particle beam irradiation apparatus that can calculate control command values without using any IF sentence (conditional expression for case classification) and enhance irradiation position precision.

Means of Solving the Problem

According to the present invention, in a particle beam irradiation apparatus for irradiating an irradiation subject with a charged particle beam accelerated by an accelerator while scanning the charged particle beam by a scanning electromagnet controlled by a scanning controller, the scanning electromagnet has an X-direction scanning electromagnet and a Y-direction scanning electromagnet for scanning in a direction perpendicular to a scanning direction of the X-direction scanning electromagnet, the scanning controller has X-direction and Y-direction inverse mapping mathematical expression models for generating each of an X-direction command value for exciting the X-direction scanning electromagnet and a Y-direction command value for exciting the Y-direction scanning electromagnet from a desired irradiation position coordinate of the charged particle beam in the irradiation subject so that irradiation to the irradiation subject so that irradiation to the irradiation subject is implemented, each of the X-direction and Y-direction inverse mapping mathematical expression models contains all of two variables when the desired irradiation position coordinate on an irradiation position plane of the charged particle beam is represented by the two variables concerned, and the X-direction and Y-direction scanning electromagnets are controlled on the basis of the X-direction and Y-direction command values generated from the desired irradiation position coordinate of the charged particle beam in the irradiation subject by the X-direction and Y-direction inverse mapping mathematical expression models, thereby irradiating the irradiation subject with the charged particle beam while scanning the charged particle beam.

Furthermore, in the particle beam irradiation apparatus, the desired irradiation position coordinate is corrected from information on movement or deformation of the irradiation subject under image pickup, and the X-direction and Y-direction scanning electromagnets are controlled on the basis of the X-direction and Y-direction command values each generated from the corrected desired irradiation position coordinate by the X-direction and Y-direction inverse mapping mathematical expression models as polynomial expressions while following the movement or the deformation of the irradiation subject, thereby irradiating the irradiation subject with the charged particle beam while scanning the charged particle beam.

Effect of the Invention

The particle beam irradiation apparatus according to this invention is provided with X-direction and Y-direction inverse mapping mathematical expression models for generating each of an X-direction command value of for exciting the X-direction scanning electromagnet and a Y-direction command value for exciting the Y-direction scanning electromagnet to implement irradiation to the irradiation subject on the basis of the desired irradiation position coordinate of the charged particle beam with respect to the irradiation subject. Each of the X-direction and Y-direction inverse mapping mathematical expression models contains all of two variables when the desired irradiation position coordinate on an irradiation position plane of the charged particle beam is represented by the two variables concerned, and the X-direction and Y-direction scanning electromagnet are controlled on the basis of the X-direction and Y-direction command values generated from the desired irradiation position coordinate of the charged particle beam in the irradiation subject by the X-direction and Y-direction inverse mapping mathematical expression models, thereby irradiating the irradiation subject with the charged particle beam while scanning the charged particle beam. Therefore, there is obtained the particle beam irradiation apparatus in which the command value for controlling the scanning electromagnet can be calculated without using any IF sentence (conditional expression for case classification), and the irradiation position precision can be enhanced since each of the X-direction and Y-direction inverse mapping mathematical expression models contains all of two variables when the desired irradiation position coordinate on an irradiation position plane of the charged particle beam is represented by the two variables concerned.

Furthermore, the desired irradiation position coordinate is corrected on the basis of the information on movement or deformation of the irradiation subject under image pickup, and X-direction and Y-direction command values are generated from the corrected desired irradiation position coordinate according to an inverse mapping mathematical expression model of the X-direction and the Y-direction as a polynomial expression. Therefore, the calculation can be quickly performed by the polynomial expression, and thus the X-direction and Y-direction scanning electromagnets can be controlled while following the movement or deformation of the irradiation subject, whereby the charged particle beam can be scanned and irradiated onto the irradiation subject.

BRIEF DESCRIPTION OF DRAWINGS

FIG. 3 is a diagram showing a calibration time in a creating method (two dimension) of the control input on the basis of the conversion table.

FIG. 12 is a diagram showing the construction of a particle beam irradiation apparatus according to a third embodiment of the present invention.

FIG. 13 is a diagram showing an operation in concert with a moving internal organ in a fourth embodiment of the present invention.

BEST MODES FOR CARRYING THE INVENTION

Figure 1A:
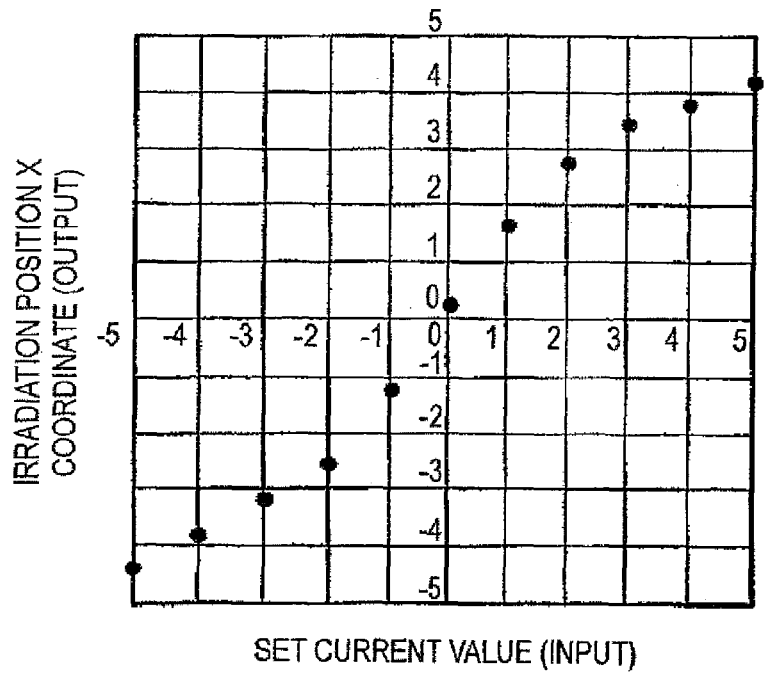
FIGS. 1A and 1B are schematic diagrams showing the relation between a control input and a control output in the case of one dimension.
Figure 1B:
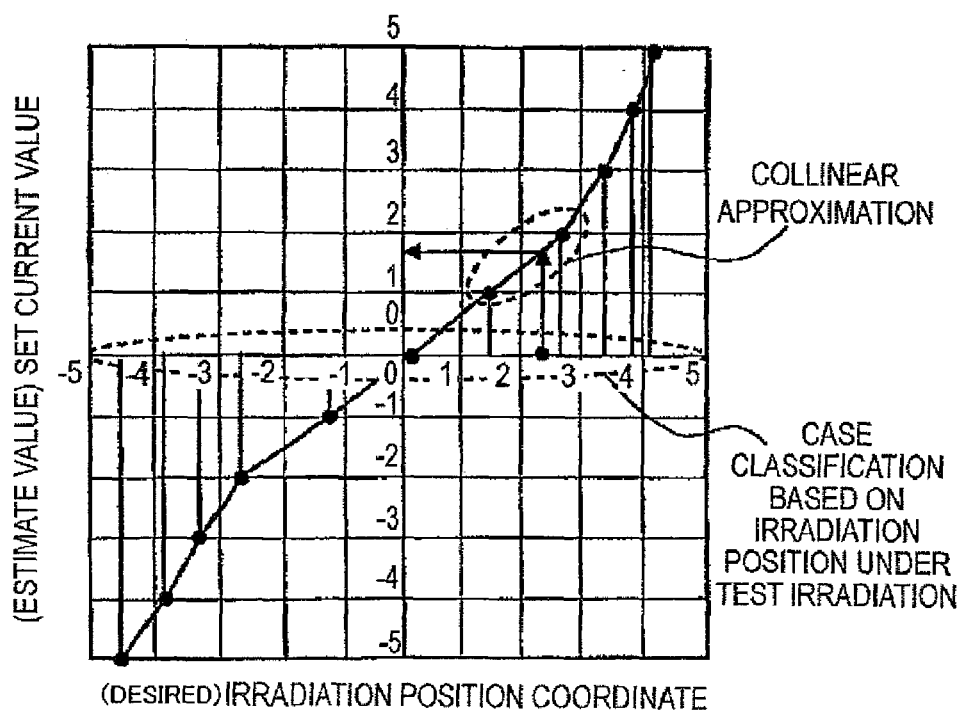

Here, the problem of the conventional particle beam irradiation apparatus using the conversion table will be reviewed in detail. First, for simplification, a case where one scanning electromagnet (scanning electromagnet) is provided to a particle beam irradiation apparatus (one-dimensional scanning in an X-direction) will be described with reference to FIGS. 1A and 1B. FIGS. 1A and 1B are schematic diagrams showing the relation between a control input and a control output in the case of one dimension. In order to enhance the precision of irradiation positions of a charged particle beam, separately from actual irradiation (treatment irradiation), test irradiation for calibration is performed under a state that no patient exists. FIG. 1A shows an example representing a test irradiation result. The abscissa axis represents a set current value for the scanning electromagnet as a control input and the ordinate axis represents an irradiation position X coordinate as a control output. When the specification of a scanning electromagnet, the specification of a power source for the scanning electromagnet and the specification of an irradiation beam (irradiation energy, incident beam position, etc.) do not vary, the irradiation position X coordinate is uniquely determined in accordance with the set current value, and thus this can be interpreted as a mapping.

Conversely, in the case of the actual irradiation (treatment irradiation), a control input (a set current value for the scanning electromagnet) must be created for a desired irradiation position coordinate. The conventional method using the conversion table will be described with reference to FIG. 1B. It should be noted that the abscissa axis and the ordinate axis of FIG. 1A counterchange each other in FIG. 1B because the input/output relation of FIG. 1A is inverted in FIG. 1B. It is assumed that a result as shown in the following table 1 is obtained between the control input (the set current value for the scanning electromagnet) and the control output (the irradiation position X coordinate) under test irradiation.

TABLE 1

Test Irradiation Result for Calibration

| Control input (set current value for scanning electromagnet) | Control output (irradiation position X coordinate) |
|---|---|
| $u_0$ | $y_0$ |
| $u_1$ | $y_1$ |
| . | . |
| . | . |
| . | . |
| $u_n$ | $y_n$ |

(here, u and y which are frequently used in the control engineering field are used as alphabets representing the control input and the control output).

If a desired irradiation position X coordinate which is required to be irradiated under actual irradiation (treatment irradiation) is accidentally equal to any irradiation position X coordinate under test irradiation, for example, when the desired irradiation position X coordinate is equal to $y_1$, the set current value for the scanning electromagnet may be set to $U_1$ from the result of the table 1. When the desired irradiation position X coordinate which is required to be irradiated under actual irradiation (treatment irradiation) is not equal to any irradiation position X coordinate under test irradiation (almost all cases correspond to this case), a method called as linear interpolation has been broadly used to calculate the corresponding set current value. The linear interpolation method will be described with reference to the flowcharts of FIG. 1B and FIG. 2.

It is assumed that the desired irradiation position X coordinate is $y_{obj}$. The desired irradiation position X coordinate $y_{obj}$ is collated with sections having boundaries at irradiation position X coordinates $y_0, y_1, \ldots, y_n$ in a test irradiation result for calibration, and it is determined which one of the sections the desired irradiation position X coordinate belongs to. When the irradiation position X coordinates $y_0, y_1, \ldots, y_n$ of the test irradiation result for calibration are arranged in order of size, the section to which the desired irradiation position X coordinate $y_{obj}$ belongs can be determined according to the method shown in the flowchart of FIG. 2. For example, when the desired irradiation position X coordinate $y_{obj}$ belongs to the section defined by $y_0$ and $y_1$, that is, in the case of $y_0 \leq y_{obj} \leq y_1$, it is assumed that the relation between the irradiation position coordinate and the set current value is linear in this section, and an estimation value $u_{obj}$ of the set current value for implementing the desired irradiation position X coordinate $y_{obj}$ is calculated by linear approximation.

[mathematical expression 1]

$$\lambda = \frac{y_{obj} - y_1}{y_0 - y_1} \quad \text{(mathematical expression 1)}$$
$$u_{obj} = \lambda u_0 + (1-\lambda)u_1$$

Figure 2:
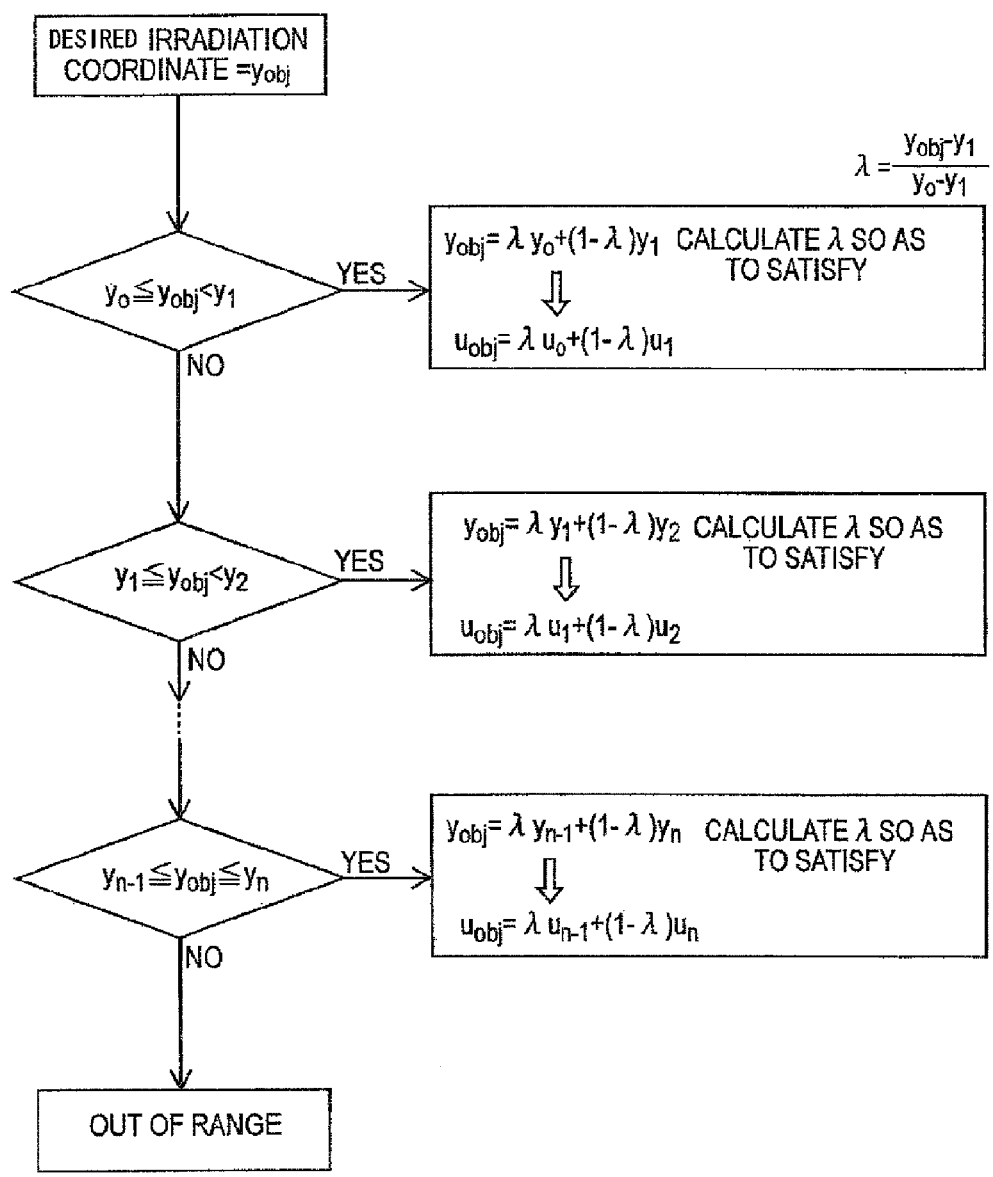
FIG. 2 is a flowchart showing a creating flow (one dimension) of a control input on the basis of a conversion table.

When the flow shown in FIG. 2 is required to be implemented, many IF sentences (conditional expressions for case classification) have been hitherto necessary in the step of specifying the section to which the desired irradiation position X coordinate $y_{obj}$ belongs.

The one-dimensional case has been described for simplification, however, the actual particle beam irradiation apparatus is required to perform two-dimensional scanning by using two scanning electromagnets. How the method using the conversion table is used in the two-dimensional case will be described with reference to FIGS. 3 and 4. The test irradiation under calibration is executed while the set current values Ia and Ib for the two scanning electromagnets $3a$, $3b$ (see FIG. 6) as a control input are varied in a lattice-shaped pattern as shown in FIG. 3($a$), for example. A control output, that is, an irradiation position coordinate for each control input is obtained as a test irradiation result as shown in FIG. 3($b$). When the specification of the scanning electromagnets, the specification of the power source for the scanning electromagnets and the specification of the irradiation beam (irradiation energy, incident beam position, etc.) are not varied, a control output is uniquely determined for each control input, and thus this can be interpreted as a mapping. Particularly, the mapping from the control input as a physical phenomenon to the control output is called as a forward mapping.

Conversely, in the case of the actual irradiation (treatment irradiation), a control input (the set current values Ia and Ib for the two scanning electromagnets) must be created for each desired irradiation position so that the desired irradiation position is implemented. A method of implementing this process by using a conversion table will be described with reference to FIGS. 4($a$) ($b$). In the one-dimensional case, sections including irradiation position X coordinates $y_0, y_1, \ldots, y_n$ of a test irradiation result for calibration as boundaries thereof are created, and it is determined which one of the sections the desired irradiation position X coordinate $y_{obj}$ belongs to. In the two-dimensional case, an irradiation position plane is divided into plural areas by polygons having irradiation position $y_0, y_1, \ldots, y_n$ of a test irradiation result for calibration as apexes thereof, and it is determined which one of the areas the desired irradiation position $y_{obj}$ belongs to.

Figure 4:
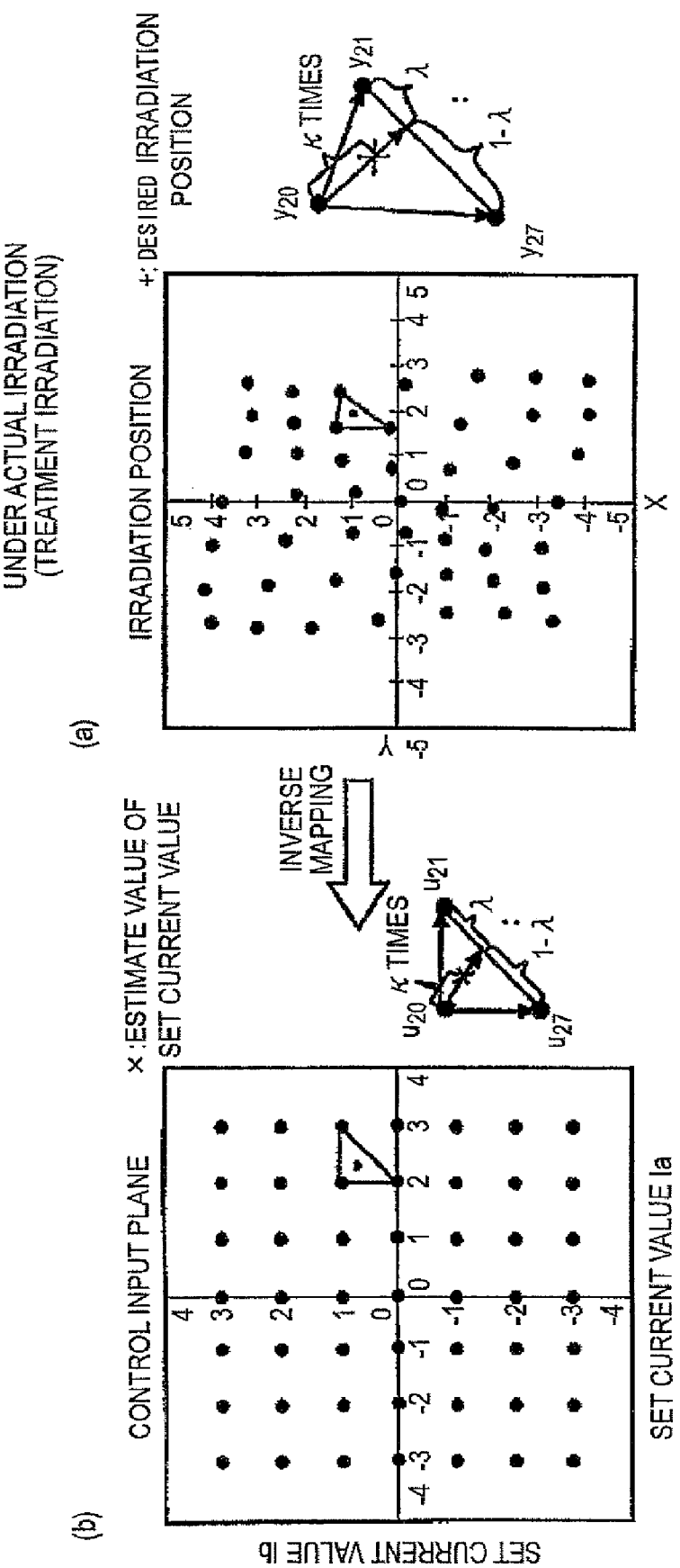
FIG. 4 is a diagram showing an actual irradiation time in the creating method (two dimension) of the control input on the basis of the conversion table.

The irradiation positions $y_0, y_1, \ldots, y_n$ of the test irradiation result and the desired irradiation position $y_{obj}$ are vectors (two-dimension). The step of determining the area to which the desired irradiation position belongs requires many IF sentences (the conditional expressions for case classification). As shown in FIG. 4($a$), it is assumed that an area to which the desired irradiation position $y_{obj}$ belongs is well determined. When $y_{20}, y_{21}, y_{27}$ represent the apexes of the area to which the desired irradiation position $y_{obj}$ belongs in the example of FIG. 4($a$), the desired irradiation position $y_{obj}$ can be represented by the following equation.

[mathematical expression 2]

$$y_{obj} = y_{20} + k\{(1-\lambda)(y_{21} - y_{20}) + \lambda(y_{27} - y_{20})\} \quad \text{(mathematical expression 2)}$$

Here, $0 \leq k \leq 1$
$0 \leq \lambda \leq 1$

[mathematical expression 3]
Or, by deforming the mathematical expression 2, $$y_{obj} = y_{20} + k\left\{\begin{array}{l}(1-\lambda)(y_{21} - y_{20}) + \\ \lambda(y_{27} - y_{20})\end{array}\right\} \quad \text{(mathematical expression 3)}$$

$$= \frac{\alpha}{(1-k)}y_{20} + \frac{\beta}{k(1-\lambda)}y_{21} + \frac{\delta}{k\lambda}y_{27}$$

$$\therefore y_{obj} = \alpha y_{20} + \beta y_{21} + \delta y_{21}$$
$$\text{and } \alpha + \beta + \delta = 1$$

here,
$0 \leq \alpha \leq 1$
$0 \leq \beta \leq 1$
$0 \leq \delta \leq 1$

The geometric meaning of the mathematical expression 2 is shown in FIG. 4($a$). When k and $\lambda$ satisfying the mathematical expression 2 are determined and they are not within the ranges of $0 \leq k \leq 1$ and $0 \leq \lambda \leq 1$, it is found that the desired irradiation position $y_{obj}$ does not belong to the area including $y_{20}$, $y_{21}$ and $y_{27}$ as the apexes. The step of determining an area to which the desired irradiation position belongs is actually performed by determining k and λ for all the areas and checking whether they are within the ranges of $0 \leq k \leq 1$ and $0 \leq \lambda \leq 1$. Here, k and λ can be calculated according to the following mathematical expression.

[mathematical expression 4]
(how to determine λ)

$$det[y_{obj} - y_{20}, y_{21} - y_{20} + \lambda(y_{27} - y_{21})] = 0 \quad \text{(mathematical expression 4)}$$

λ satisfying the mathematical expression 4 is calculated. The matrix of the mathematical expression 4 is represented as the following form by substituting specific coordinates of $y_{20}$, $y_{21}$, $y_{27}$ and $y_{obj}$ into the mathematical expression 4.

$$det\begin{bmatrix} x_{obj-20}, & x_{21-20} + \lambda x_{27-21} \\ y_{obj-20}, & y_{21-20} + \lambda y_{27-21} \end{bmatrix} = 0 \quad \text{(mathematic expression 5)}$$

$$\Rightarrow x_{obj-20}(y_{21-20} + \lambda y_{27-21}) -$$
$$(x_{21-20} + \lambda x_{27-21})y_{obj-20} = 0$$
$$\Rightarrow \lambda(x_{obj-20} y_{27-21} - x_{27-21} y_{obj-20}) +$$
$$x_{obj-20} y_{21-20} - x_{21-20} y_{obj-20} = 0$$
$$\Rightarrow \therefore \lambda = \frac{x_{obj-20} y_{21-20} - x_{21-20} y_{obj-20}}{x_{obj-20} y_{27-21} - x_{27-21} y_{obj-20}}$$

[mathematical expression 6]
(how to determine k)
λ calculated according to the mathematical expression 5 is used.

$$p = y_{obj} - y_{20} \quad \text{(mathematical expression 6)}$$
$$q = y_{21} - y_{20} + \lambda(y_{27} - y_{21})$$
$$k = \frac{|p|}{|q|}$$

Here, ‖ represents the magnitude of vector, and $|p| = \sqrt{p^T p}$.

Figure 5:
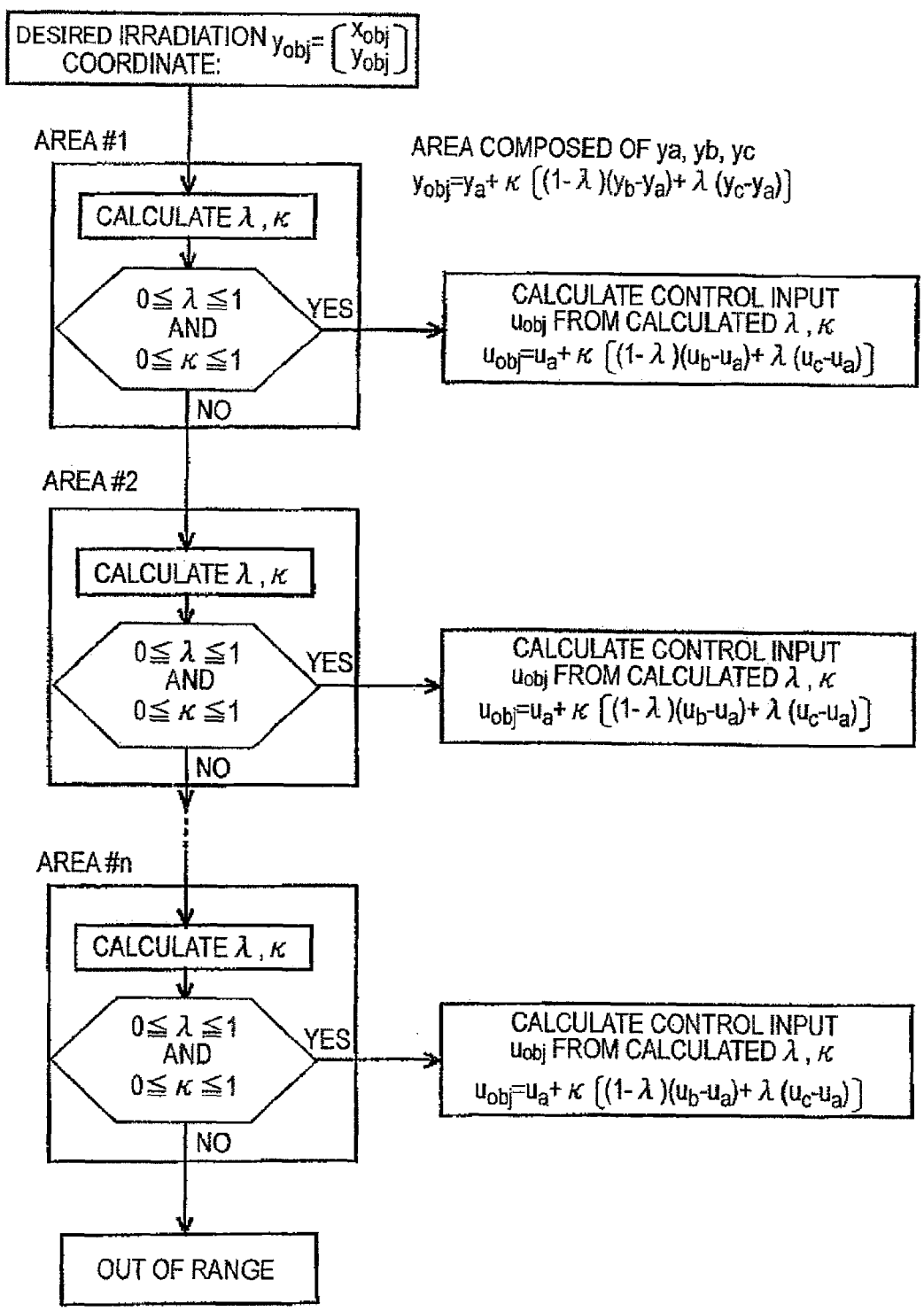
FIG. 5 is a flowchart showing the creating flow (two dimension) of the control input on the basis of the conversion table.

As described above, according to the method using the conversion table, k and λ are calculated for all the areas to determine an area to which the desired irradiation coordinate belongs, and thus this method has a problem that many calculations and many IF sentences (the conditional expressions for case classification) are required. (see FIG. 5: flowchart of two dimension)

First Embodiment

Figure 6:
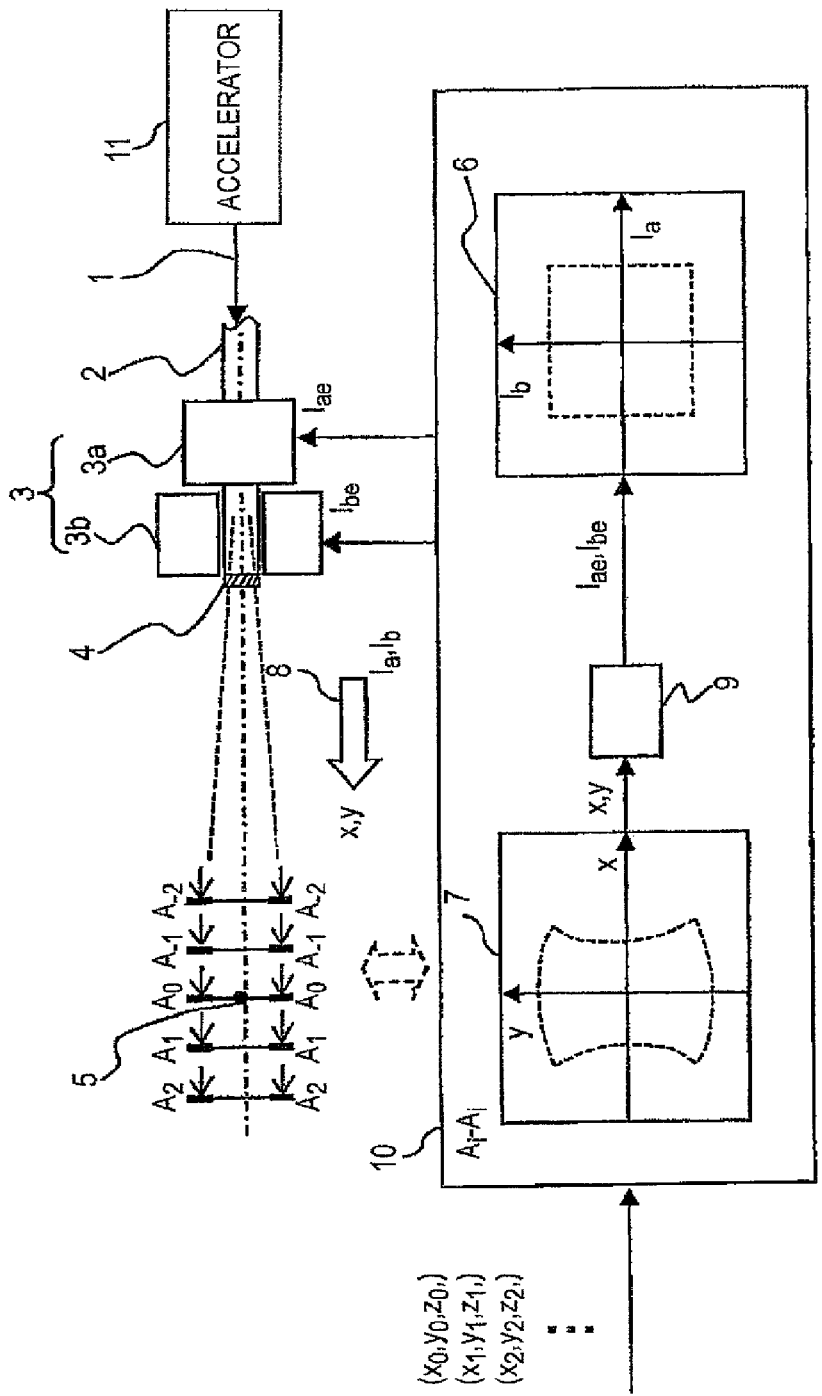
FIG. 6 is a diagram showing the construction of a particle beam irradiation apparatus according to a first embodiment 1 of the present invention.

FIG. 6 is a diagram showing the configuration of a particle beam irradiation apparatus for performing scanning irradiation according to a first embodiment of the present invention. The particle beam irradiation apparatus has an accelerator 11 for accelerating a charged particle beam 1 to obtain a charged particle beam 1 having desired kinetic energy, a beam transport duct 2 for transporting the charged particle beam 1, a scanning electromagnet (scanning electromagnet) 3 for scanning the charged particle beam 1, a beam outlet window 4 for picking up a beam, a scanning controller 10 for transmitting an command value to the scanning electromagnet 3, etc. A beam transport system having the beam transport duct 2 is provided with a bending electromagnet, a beam monitor, a shielding electromagnet, a beam damper, an irradiation path bending electromagnet, etc. In the particle beam irradiation apparatus according to the first embodiment, the scanning controller 10 has an inverse mapping mathematical expression model for a mapping from a beam irradiation position coordinate space 7 to a scanning electromagnet command value space 6. In other words, the scanning controller 10 has inverse mapping means 9 for generating, for a desired beam irradiation position coordinate, an estimation value of an command value for the scanning electromagnet 3 to implement the irradiation to the desired beam irradiation position coordinate concerned.

Next, the operation of the particle beam irradiation apparatus will be described. The charged particle beam 1 which has been accelerated to have a desired kinetic energy by the accelerator 11 is passed through the beam transport duct 2 and led to an irradiation unit. The charged particle beam 1 is further picked up through the beam outlet window 4, and irradiated to an isocenter 5 as an irradiation reference point. In general, in order to selectively scan and irradiate a diseased site as an irradiation subject, the X and Y directions of the beam irradiation position of the charged particle beam 1 are generally controlled by an X-direction scanning electromagnet (X-direction scanning electromagnet) 3a and a Y-direction scanning electromagnet (Y-direction scanning electromagnet) 3b provided to the outside of the beam transport duct 2, and also the kinetic energy of the charged particle beam 1 is varied by the accelerator 11, whereby the Z-direction of the beam irradiation position (the depth direction of the diseased site) is controlled. The beam irradiation position is controlled according to a method of executing central control with an irradiation control device 23 (see FIG. 10) for controlling the overall particle beam irradiation apparatus or a method of executing distributed control with the scanning controller 10 for controlling the scanning electromagnet and the kinetic energy of the charged particle beam 1 of the accelerator.

In the first embodiment, the scanning controller 10 for controlling the irradiation position of the charged particle beam 1 is provided with the inverse mapping means 9 having the inverse mapping mathematical expression model from the beam irradiation position coordinate space 7 to the scanning electromagnet command value space 6. A preferable example of the inverse mapping mathematical expression model is a polynomial expression model comprising desired irradiation position coordinates. A polynomial expression for the maximum order=2 is represented by the following mathematical expression 7. In the first embodiment, the Z-direction (depth direction) of the beam irradiation position is assumed to be uniquely determined by the kinetic energy of the charged particle beam, and plural inverse mapping mathematical expression models (that is, X-direction and Y-direction inverse mapping mathematical expression models) are created for different kinetic energies.

[mathematical expression 7]

$$\begin{cases} I_{ae} = a_{00} + a_{01}x + a_{02}x^2 + \\ \quad a_{10}y + a_{11}xy + a_{20}y^2 \\ I_{be} = b_{00} + b_{01}x + b_{02}x^2 + \\ \quad b_{10}y + b_{11}xy + b_{20}y^2 \end{cases}$$ (mathematical expression 7)

Here, $a_{00}, a_{01}, a_{02}, \ldots, b_{00}, b_{01}, b_{02}, \ldots$ represent coefficients (unknown parameters) for determining the characteristic of the inverse mapping mathematical expression model. $I_{ae}$ (X-direction command value) and $I_{be}$ (Y-direction command value) are estimated values of the command values for the X,Y-direction scanning electromagnets when the irradiation position coordinate of the charged particle beam is (x,y). That is, each of the X-direction and Y-direction inverse mapping mathematical expression model (mathematical expression 7) for generating the X-direction command value $I_{ae}$ and the Y-direction command value $I_{be}$ contains all of two variables (x,y) when the desired irradiation position coordinate on the irradiation position plane of the charged beam is represented by the two variables (x,y). The coefficients (unknown parameters) for determining the characteristic of the inverse mapping mathematical expression model may be determined by performing test irradiation for calibration (calibration) in advance and applying the least square method on the actual data of the test irradiation or the like.

Figure 7:
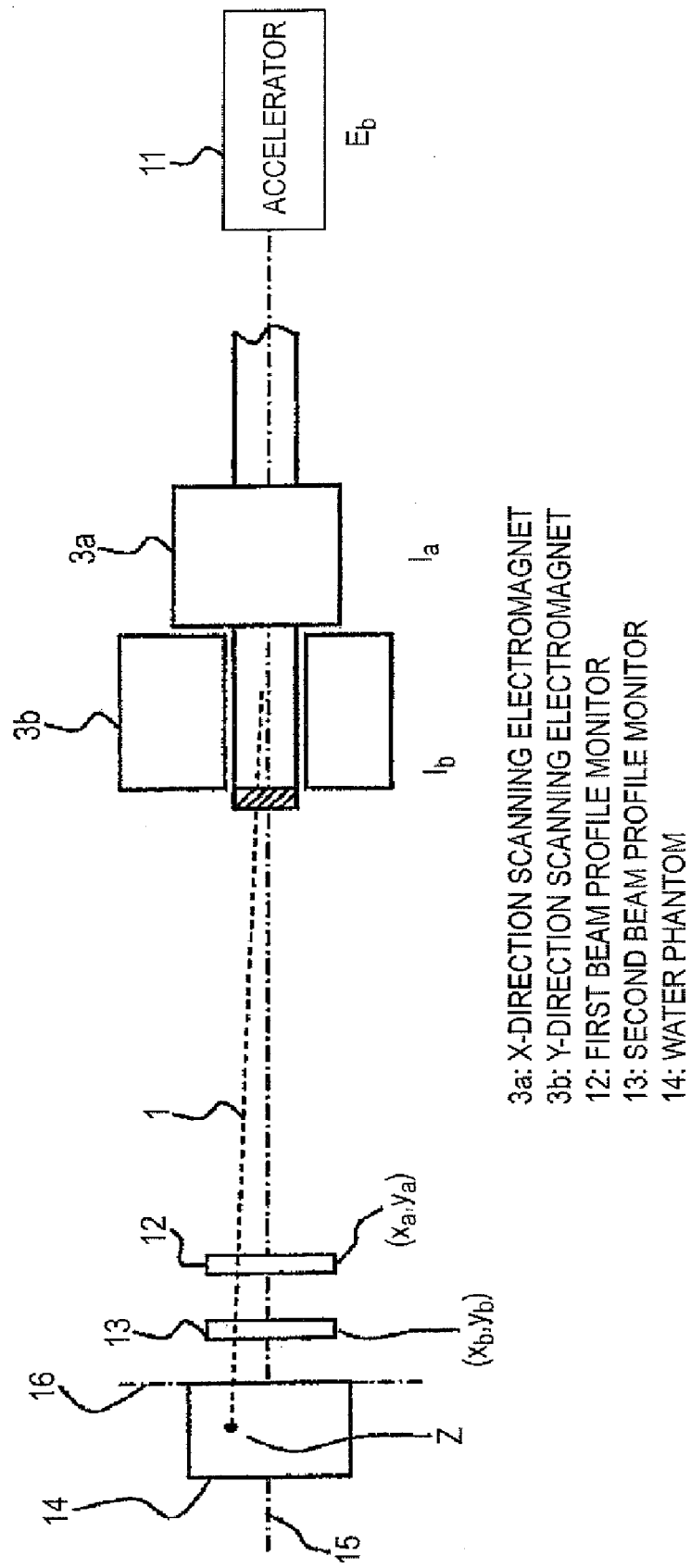
FIG. 7 is a diagram showing a method of calculating coefficients (unknown parameters) from actual data at the calibration time in the present invention.
Figure 8:
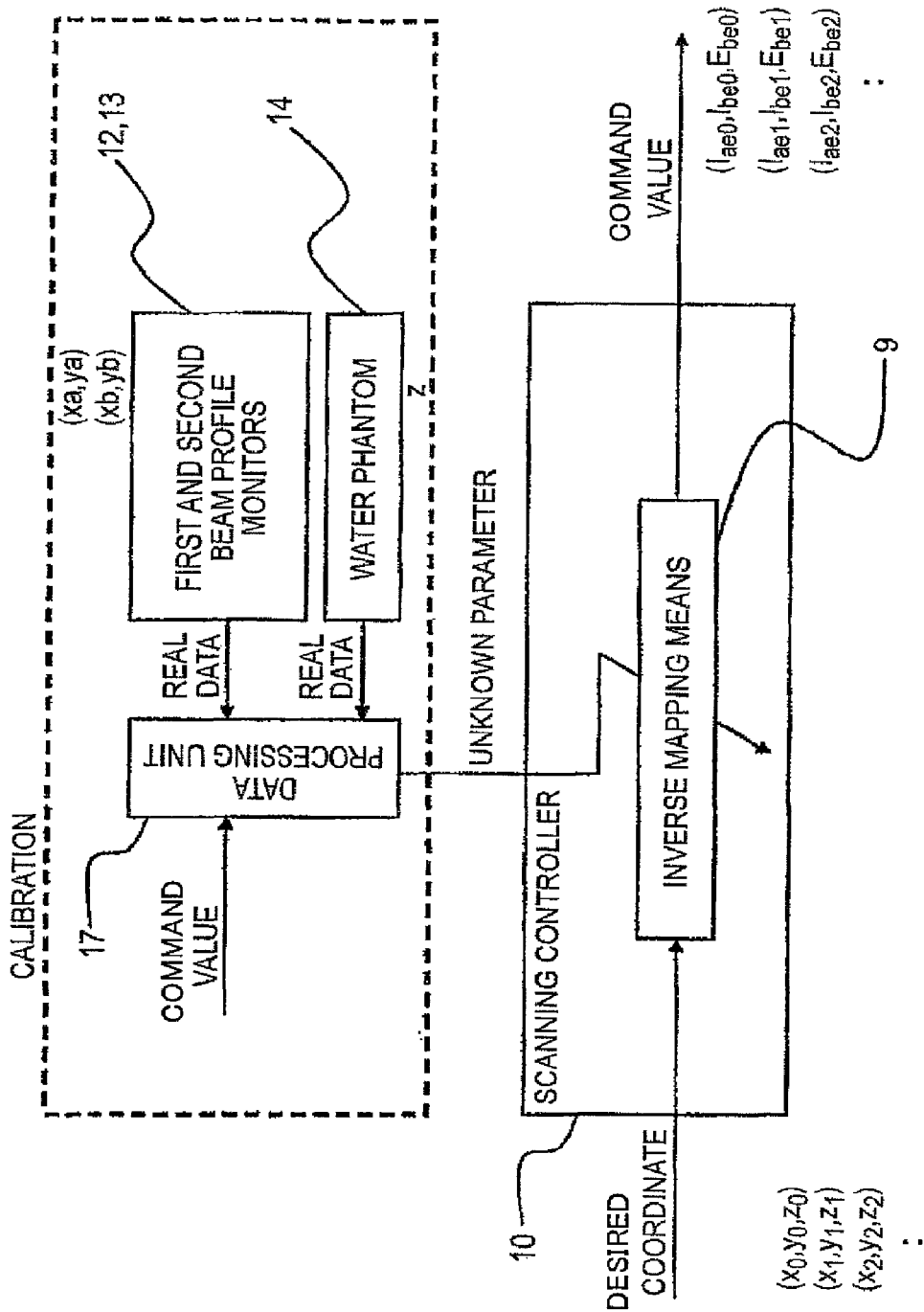
FIG. 8 is a block diagram showing the method of calculating the coefficients (unknown parameters) in the present invention.
Figure 9:
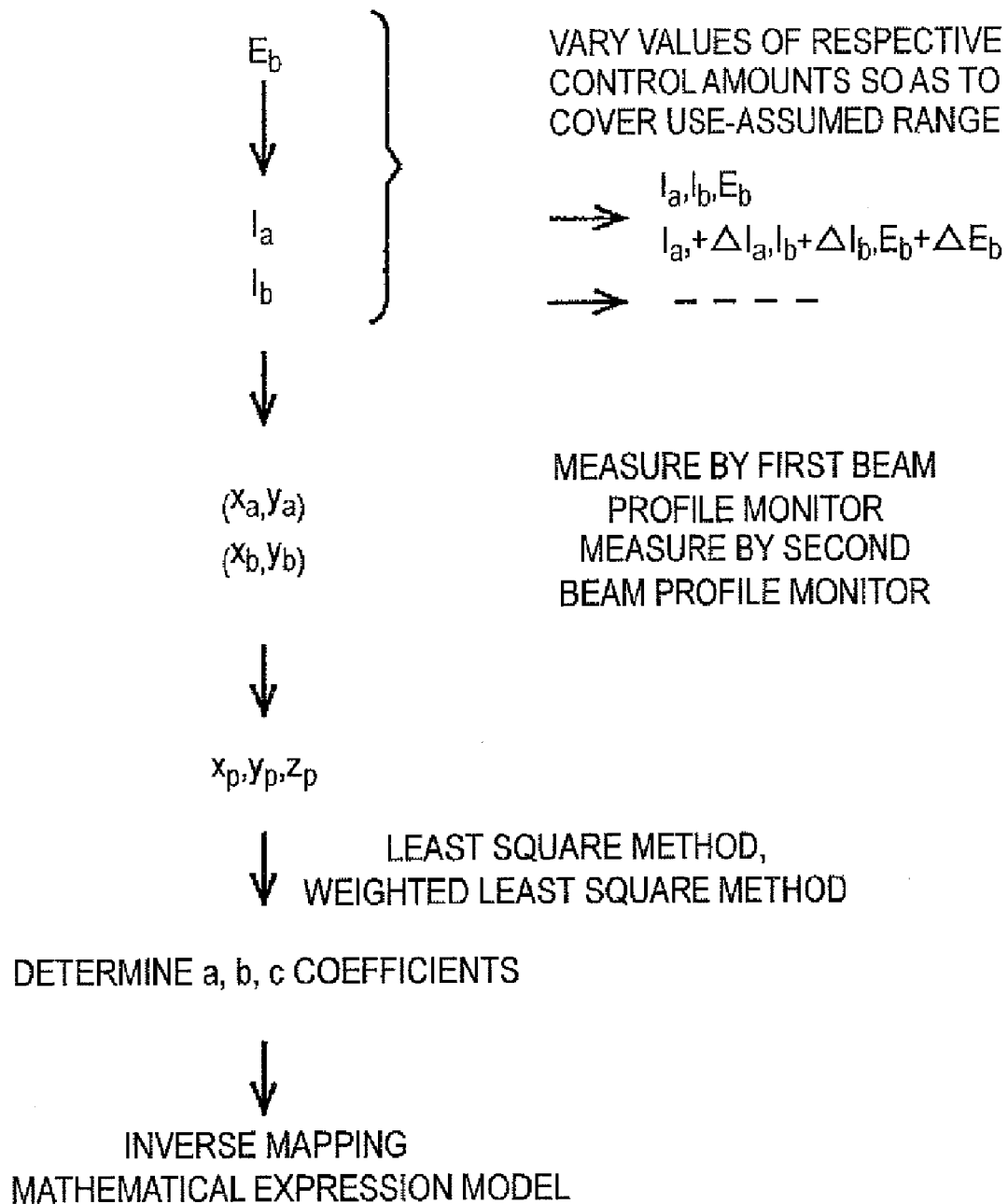
FIG. 9 is a flowchart showing the method of calculating the coefficients (unknown parameters) in this invention.

FIG. 7 is a diagram showing a method of calculating the coefficients (unknown parameters) from the actual data obtained under the calibration. In FIG. 6, 8 represents the direction of a forward mapping (actual physical phenomenon). FIG. 8 is a block diagram showing the method of calculating the coefficients (unknown parameters). FIG. 9 is a flowchart showing the method of calculating the coefficients (unknown parameters). In each figure, the same reference numerals represent same or corresponding parts. In the figures, 12 represent a first beam profile monitor, and it is disposed vertically to a reference irradiation axis 15 of the charged particle beam, and outputs the two-dimensional passage position coordinate ($x_a$, $y_a$) of the charged particle beam to be irradiated. 13 represents a second beam profile monitor, and it is disposed vertically to the reference irradiation axis 15 of the charged particle beam so as to be spaced from the first beam profile monitor 12 at a predetermined interval, and outputs the two-dimensional passage position coordinate ($x_b$, $y_b$) of the charged particle beam to be irradiated. 14 represents a water phantom, and it is disposed vertically to the reference irradiation axis 15 so that the surface thereof is fit to the body surface 16 of a patient, and outputs the coordinate $z_p$ in the depth direction of the position coordinate which the charged particle beam to be irradiated reaches. The first and second beam profile monitors 12 and 13 and the water phantom 14 are arranged when the unknown parameters are calculated or the charged particle beam is corrected or checked, and moved when the patient is irradiated with the charged particle beam.

The test irradiation for calibration is executed while the following values are fluctuated by the scanning controller 10.

Command value $I_a$ for the X-direction scanning electromagnet (=current value, current value calculated and corrected in consideration of hysteresis, set magnetic field intensity, etc.)

Command value $I_b$ for the Y-direction scanning electromagnet (=current value, current value calculated and corrected in consideration of hysteresis, set magnetic field intensity, etc.)

Kinetic energy command value $E_b$ for accelerator

The charged particle beam 1 which is irradiated upon reception of the command values passes through the first and second beam profile monitors 12 and 13, and the measured passage position coordinates ($x_a$, $y_a$), ($x_b$, $y_b$) are output from the first and second beam profile monitors 12 and 13. It is also assumed that the depth-direction coordinate z which the irradiated charged particle beam 1 reaches is uniquely determined on the basis of the kinetic energy of the charged particle. Data processing means 17 (FIG. 8) calculates the irradiation position coordinate (x,y,z) from these values ($x_a$, $y_a$), ($x_b$, $y_b$) and z.

As described above, the test irradiation for calibration is executed by fluctuating the respective command values. For example, the command value $I_a$ for the X-direction scanning electromagnet is fluctuated to $I_a+\Delta I_a, \ldots$, and the command value $I_b$ for the Y-direction scanning electromagnet is fluctuated to $I_b+\Delta I_b, \ldots$. Here, an example of a method of determining the coefficients (unknown parameters) of an inverse mapping from the actual data of the test irradiation will be described. The polynomial expression model shown in the mathematical expression 7 can be represented by using a matrix and vectors.

[mathematical expression 8]

$$\underbrace{\begin{bmatrix} 1 & x & x^2 & y & xy & y^2 \end{bmatrix}}_{Ac} \underbrace{\begin{bmatrix} a_{00} & b_{00} \\ a_{01} & b_{01} \\ a_{02} & b_{02} \\ a_{10} & b_{10} \\ a_{11} & b_{11} \\ a_{20} & b_{20} \end{bmatrix}}_{Xc} = \underbrace{\begin{bmatrix} I_{ae} & I_{be} \end{bmatrix}}_{Be}$$ (mathematical expression 8)

Here, the matrix Ac is an input matrix of the inverse mapping including the irradiation position coordinates, a matrix Xc represents an unknown parameter matrix of the inverse mapping, and a matrix Be represents an output matrix of the inverse mapping including estimation values of the command values. The values of the unknown parameter matrix Xc have not yet been determined at this stage. The command values Bcarib for the test irradiation for calibration and the actual data of the irradiation positions Acarib are arranged according to the form of the mathematical expression 8 so as to form a vertically long matrix.

[mathematical expression 9]

$$\underbrace{\begin{bmatrix} 1 & x_0 & x_0^2 & y_0 & x_0 y_0 & y_0^2 \\ 1 & x_1 & x_1^2 & y_1 & x_1 y_1 & y_1^2 \\ \vdots & \vdots & \vdots & \vdots & \vdots & \vdots \\ 1 & x_n & x_n^2 & y_n & x_n y_n & y_n^2 \end{bmatrix}}_{A_{carib}} \underbrace{\begin{bmatrix} a_{00} & b_{00} \\ a_{01} & b_{01} \\ a_{02} & b_{02} \\ a_{10} & b_{10} \\ a_{11} & b_{11} \\ a_{20} & b_{20} \end{bmatrix}}_{X_c} = \underbrace{\begin{bmatrix} I_{a0} & I_{b0} \\ I_{a1} & I_{b1} \\ \vdots & \vdots \\ I_{an} & I_{bn} \end{bmatrix}}_{B_{carib}}$$

(mathematical expression 9)

Here, the subscript numeral means the test irradiation number for calibration (in the above example, it means that test irradiation for n places is executed). The unknown parameter matrix Xc of the inverse mapping is determined according to the following expression based on the least square method.

[mathematical expression 10]

$$Xc = (A_{carib}^T A_{carib})^{-1} A_{carib}^T B_{carib}$$  (mathematical expression 10)

Here, the superscript T represents a transposed matrix.

After the respective coefficients of the polynomial expression are determined through the above calibration, the actual irradiation is executed. First, it is checked by the beam monitor (not shown) provided to the beam transport duct 1 whether the beam incident point to the scanning electromagnet 3a does not vary from that under the calibration. At this time, when it is found that the beam incident point varies, the calibration procedure may be executed again to determine the respective coefficients.

The order of the polynomial expression model of the mathematical expression 7, etc. may be properly increased in accordance with the characteristic of the particle beam irradiation apparatus being handled when it has strong non-linearity, and the order is not limited to the order=2 indicated in the mathematical expression 7. Some polynomial expression models (inverse mapping mathematical expression models) may be prepared in advance so that an operator can select any polynomial expression model. Furthermore, the inverse mapping mathematical expression model may be a mathematical expression other than the polynomial expression insofar as the mathematical expression can approximate.

The particle beam irradiation apparatus is required to irradiate a charged particle beam three-dimensionally, and the desired beam irradiation position coordinate (x,y,z) is generally transmitted to the scanning controller 10 in the form of $(x_0, y_0, z_0) (x_1, y_1, z_1) (x_2, y_2, z_2), \ldots$ as shown in FIG. 6.

Figure 10:
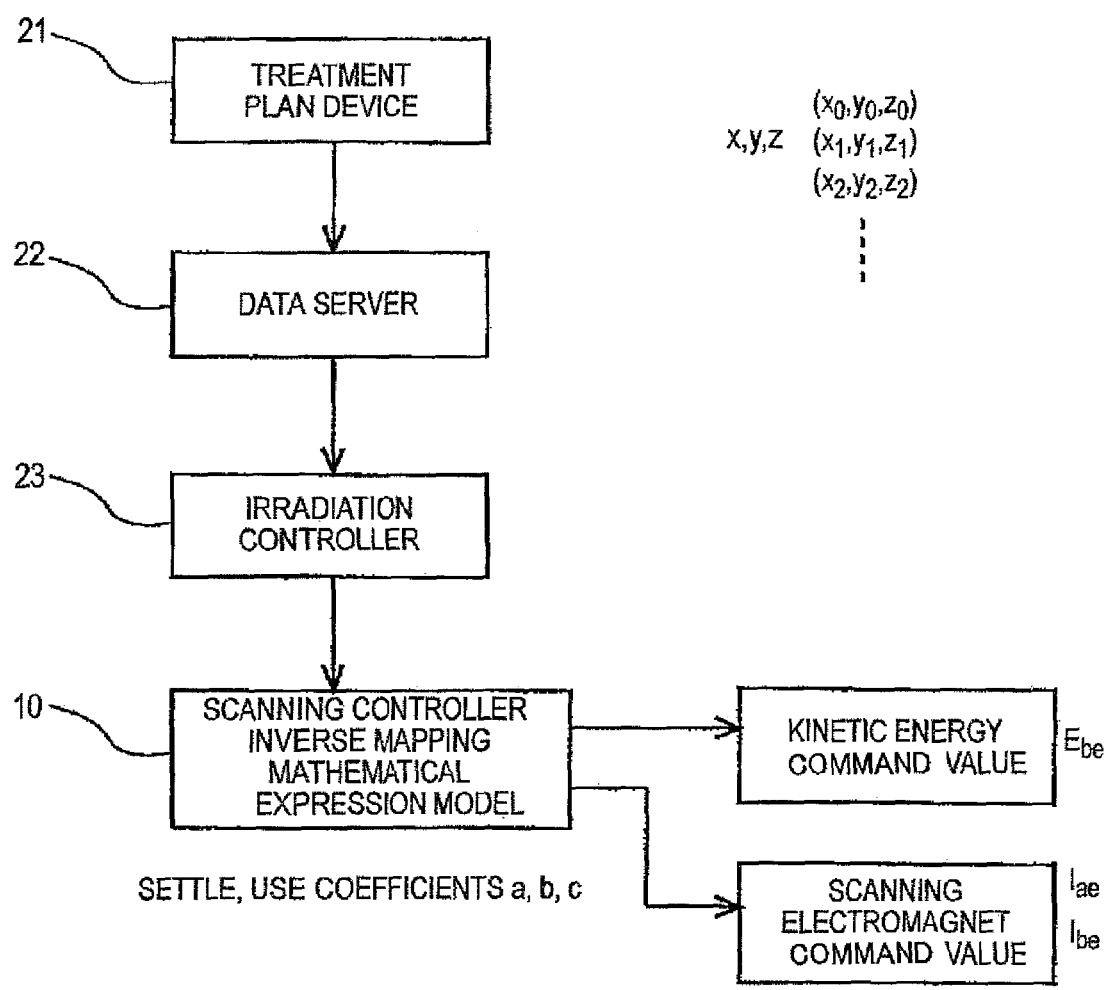
FIG. 10 is a block diagram for determining an command value of a scanning electromagnet and an command value of kinetic energy of a charged particle beam from a treatment plan value in the present invention.

FIG. 10 is a block diagram to determine the command values for the scanning electromagnets and the command value for the kinetic energy of the charged particle beam on the basis of treatment plan values. The desired beam irradiation position coordinates $(x_0, y_0, z_0) (x_1, y_1, z_1) (x_2, y_2, z_2), \ldots$ are transmitted through a data server 22 and the irradiation control device 23 to the scanning controller 10 by a treatment plan device 21 for a patient. The inverse mapping mathematical expression model and the kinetic energy command value $E_{be}$ in FIG. 10 will be described with reference to a second embodiment. The first embodiment does not contain the control in the Z direction of the beam irradiation position with the kinetic energy of the charged particle beam of the accelerator set as a set value. Accordingly, when the beam incident point to the scanning electromagnet 3a is set not to vary, the desired beam irradiation position coordinates $(x_0, y_0) (x_1, y_1) (x_2, y_2), \ldots$ are substituted into the inverse mapping mathematical expression model (mathematical expression 7) of the scanning controller 10, and the estimation values $(I_{ae}, I_{be}), \ldots$ of the scanning electromagnet command values are calculated for the respective desired beam irradiation position coordinates.

In the first embodiment, the inverse mapping is determined for each of the plural different charged particle beam kinetic energies. Specifically, there are prepared not only the inverse mapping mathematical expression model for the mapping to a plane $A_0$-$A_0$ containing the isocenter 5 as the irradiation reference, but also inverse mapping mathematical expression models for mappings to planes $A_{-1}$-$A_{-1}$, $A_{-2}$-$A_{-2}$, ... which are fixed in front of the isocenter 5 by changing the kinetic energy of the charged particle beam every $-\Delta E_b$, (it is unnecessary to fluctuate at even intervals) and inverse mapping mathematical expression models for mappings to $A_1$-$A_1$, $A_2$-$A_2$, ... which are fixed at the backside of the isocenter 5 by changing the kinetic energy of the charged particle beam every $+\Delta E_b$. When the beam irradiation position coordinate in the irradiation subject is located between planes, linear interpolation is executed.

As described above, the first embodiment is provided with the calculating means (inverse mapping means) for calculating estimation values $(I_{ae}, I_{be})$ of the command values for the scanning electromagnets to implement the irradiation with respect to the desired irradiation position coordinate (x,y) on the irradiation reference plane so that the irradiation at the desired irradiation position coordinate (x,y) on the irradiation reference plane is implemented. Specifically, the inverse mapping means has a polynomial expression model of 2-input and 2-output. Therefore, according to this embodiment, there can be obtained the high-precision and high-reliability particle beam irradiation apparatus which does not require many calculations and many IF sentences (conditional expressions for case classification) to determine an area to which the desired irradiation coordinate belongs from many areas created on the basis of calibration data as in the case of use of the conversion table, and compensates the beam position precision in accordance with the individual difference of the particle beam irradiation apparatus as a target, use environment and secular variation.

Second Embodiment

Figure 11:
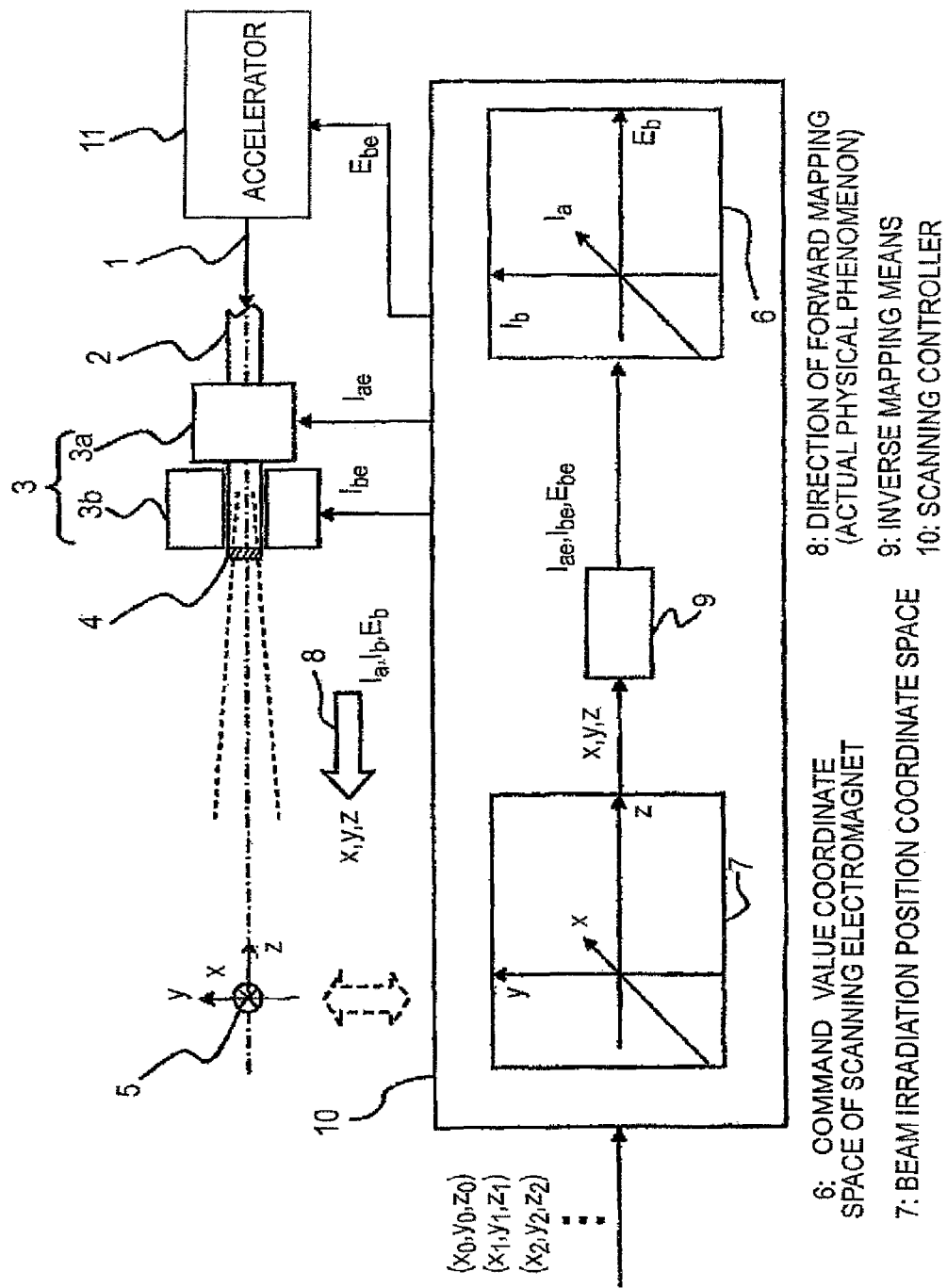
FIG. 11 is a diagram showing the construction of a particle beam irradiation apparatus according to a second embodiment of the present invention.

FIG. 11 is a diagram showing the construction of a particle beam irradiation apparatus according to a second embodiment. In the first embodiment, the inverse mapping mathematical expression model is treated as a 2-input 2-output model. However, in the second embodiment, the inverse mapping mathematical expression model is treated as a 3-input 3-output model as shown in FIG. 11 and the following mathematical expression 11 (described later). The following mathematical expression 11 represents a polynomial expression model comprising desired irradiation position coordinates in the case of 3-input, 3-output and the maximum order=2.

[mathematical expression 11]

$$\begin{cases} I_{ae} = a_{000} + a_{001}x + a_{002}x^2 + \\ \quad a_{010}y + a_{011}xy + a_{020}y^2 + \\ \quad a_{100}z + a_{101}xz + a_{110}yz + a_{200}z^2 \\ I_{be} = b_{000} + b_{001}x + b_{002}x^2 + \\ \quad b_{010}y + b_{011}xy + b_{020}y^2 + \\ \quad b_{100}z + b_{101}xz + b_{110}yz + b_{200}z^2 \\ E_{be} = c_{000} + c_{001}x + c_{002}x^2 + \\ \quad c_{010} + c_{011}xy + c_{020}y^2 + \\ \quad c_{100}z + c_{101}xz + c_{110}yz + c_{200}z^2 \end{cases}$$ (mathematical expression 11)

Here, $a_{000}$, $a_{001}$, $a_{002}$, ..., $b_{000}$ $b_{001}$, $b_{002}$, ..., $c_{000}$, $c_{001}$, $c_{002}$, ..., represent coefficients (unknown parameters) for determining the characteristic of the inverse mapping mathematical expression model. $I_{ae}$, $I_{be}$, $E_{be}$ represent estimation values of command values for the X, Y-direction scanning magnets and an estimation value of an command value of the kinetic energy of the charged particle beam for the accelerator when the irradiation position coordinate of the charged particle beam is represented by (x,y,z). As in the case of the first embodiment, the coefficients (unknown parameters) for determining the characteristic of the inverse mapping mathematical expression model are determined by executing test irradiation for calibration (calibration) and applying the least square method or the like on the actual data of the test irradiation.

The test irradiation for calibration is executed by fluctuating the following values with the scanning controller 10.

Command value $I_a$ for the X-direction scanning electromagnet (=current value, current value calculated and corrected in consideration of hysteresis, set magnetic field intensity, etc.)

Command value $I_b$ for the Y-direction scanning electromagnet (=current value, current value calculated and corrected in consideration of hysteresis, set magnetic field intensity, etc.)

Kinetic energy command value $E_b$ for accelerator

Upon reception of the command values, the irradiated charged particle beam 1 passes through the first and second beam profile monitors 12, 13, and measured passage position coordinates $(x_a, y_a)$, $(x_b, y_b)$ are output from the first and second beam profile monitors 12 and 13 as shown in FIGS. 7, 8 and 9. Furthermore, the irradiated charged particle beam 1 arrives at the water phantom 14, and the coordinate $z_p$ in the depth direction of the position coordinate at which it arrives is output. The data processing means 17 (FIG. 3) which obtains these output values determines $(x_p, y_p)$ of the arrival position coordinate from $(x_a, y_a)$, $(x_b, y_b)$ and $z_p$, and determines the arrival position coordinate $(x_p, y_p, z_p)$.

As described above, the test irradiation for calibration is executed by fluctuating the value of each command value. For example, the command value $I_a$ for the X-direction scanning electromagnet is fluctuated to $I_a + \Delta I_a$, ..., the command value $I_b$ for the Y-direction scanning electromagnet is fluctuated to $I_b + \Delta I_b$, ..., and the kinetic energy command value $E_b$ for the accelerator is fluctuated to $E_b + \Delta E_b$, .... Here, an example of a method of determining the coefficients (unknown parameters) of the inverse mapping in the case of 3-input and 3-output from the actual data of the test irradiation will be described. The polynomial expression model shown in the mathematical expression 11 can be represented as follows by using a matrix and vectors.

[mathematical expression 12]

(mathematical expression 12)

$$\underbrace{\begin{bmatrix} 1 & x & x^2 & y & xy & y^2 & z & xz & yz & z^2 \end{bmatrix}}_{Ac} \underbrace{\begin{bmatrix} a_{000} & b_{000} & c_{000} \\ a_{001} & b_{001} & c_{001} \\ a_{002} & b_{002} & c_{002} \\ a_{010} & b_{010} & c_{010} \\ a_{011} & b_{011} & c_{011} \\ a_{020} & b_{020} & c_{020} \\ a_{100} & b_{100} & c_{100} \\ a_{101} & b_{101} & c_{101} \\ a_{110} & b_{110} & c_{110} \\ a_{200} & b_{200} & c_{200} \end{bmatrix}}_{Xc} = \underbrace{\begin{bmatrix} I_{ae} & I_{be} & E_{be} \end{bmatrix}}_{Be}$$

Here, the matrix Ac represents an input matrix of the inverse mapping comprising the irradiation position coordinates, the matrix Xc represents an unknown parameter matrix of the inverse mapping, and the matrix Be represents an output matrix of the inverse mapping comprising estimation values of command values. The values of the unknown parameter matrix Xc have not yet been determined at this stage. The command values obtained in the test irradiation for calibration and the actual data of the irradiation positions are arranged according to the form of the mathematical expression 12 so as to form a vertically long matrix. The command values Bcarib in the case of the test irradiation for calibration and the actual data of the obtained irradiation positions Acarib are arranged vertically according to the form of the mathematical expression 12 so as to form a vertically long matrix.

[mathematical expression 13]

(mathematical expression 13)

$$Acarib = \begin{bmatrix} 1 & x_0 & x_0^2 & y_0 & x_0y_0 & y_0^2 & z_0 & x_0z_0 & y_0z_0 & z_0^2 \\ 1 & x_1 & x_1^2 & y_1 & x_1y_1 & y_1^2 & z_1 & x_1z_1 & y_1z_1 & z_1^2 \\ \vdots & \vdots & \vdots & \vdots & \vdots & \vdots & \vdots & \vdots & \vdots & \vdots \\ 1 & x_n & x_n^2 & y_n & x_ny_n & y_n^2 & z_n & x_nz_n & y_nz_n & z_n^2 \end{bmatrix}$$

$$Xc = \begin{bmatrix} a_{000} & b_{000} & c_{000} \\ a_{001} & b_{001} & c_{001} \\ a_{002} & b_{002} & c_{002} \\ a_{010} & b_{010} & c_{010} \\ a_{011} & b_{011} & c_{011} \\ a_{020} & b_{020} & c_{020} \\ a_{100} & b_{100} & c_{100} \\ a_{101} & b_{101} & c_{101} \\ a_{110} & b_{110} & c_{110} \\ a_{200} & b_{200} & c_{200} \end{bmatrix} = Bcarib = \begin{bmatrix} I_{a0} & I_{b0} & E_{b0} \\ I_{a1} & I_{b1} & E_{b1} \\ \vdots & \vdots & \vdots \\ I_{a_n} & I_{b_n} & E_{b_n} \end{bmatrix}$$

Here, the subscript numeral means the test irradiation number of calibration (in the above example, it means that the test irradiation for (n+1) places is executed). The unknown parameter matrix Xc of the inverse mapping is determined by the mathematical expression 10 based on the least square method as in the case of the first embodiment. After the respective coefficients of the polynomial expression is determined by the above calibration, the actual irradiation is executed. First, it is checked by the beam monitor (not shown) provided to the beam transport duct 1 that the beam incident point to the scanning electromagnet 3a does not vary from that at the calibration time. At this time, when it is found that the beam incident point varies, the calibration procedure may be executed again to determine the respective coefficients.

The order of the polynomial expression model as the inverse mapping mathematical expression mode may be properly increased in accordance with the characteristic of the particle beam irradiation apparatus being handled when it has strong non-linearity, and the order is not limited to the order=2 indicated in the mathematical expression 11. In the second embodiment, some polynomial expression models may be also prepared in advance so that an operator can select any polynomial expression model.

In the second embodiment, the desired beam irradiation position coordinates $(x_0, y_0, z_0) (x_1, y_1, z_1) (x_2, y_2, z_2) \ldots$ are also transmitted through the data server 22 and the irradiation control device 23 to the scanning controller 10 by the treatment plan device 21 for a patient as shown in FIG. 10. When the beam incident point to the scanning electromagnet 3a is set not to vary, the transmitted desired beam irradiation position coordinates $(x_0, y_0, z_0) (x_1, y_1, z_1) (x_2, y_2, z_2) \ldots$ are substituted into the inverse mapping mathematical expression model (mathematical expression 11) of the scanning controller 10, and the estimation values $(I_{ae}, I_{be}) \ldots$ of the command values for the scanning electromagnets and the estimation values $(E_{be}) \ldots$ of the kinetic energy command values are calculated for the respective desired beam irradiation position coordinates.

The position control of the charged particle beam is roughly performed by the scanning electromagnet 3 for the X and Y directions and by the adjustment of the kinetic energy of the charged particle beam for the Z direction. However, strictly, the control cannot be so clearly divided into XY and Z. When the charged particle beam is controlled by the scanning electromagnet 3, it affects not only the XY directions, but also the Z direction. Likewise, when the kinetic energy of the charged particle beam is controlled, not only the Z direction, but also the XY directions may be affected. Such an effect as described above is referred to as "interference term effect between XY and Z. The inverse mapping mathematical expression model of 3-input and 3-output can generate the command values in consideration of the interference term effect between XY and Z.

In the conventional methods based on deflection correction (for example, patent document 1), no attention is paid to the Z direction. However, according to the second embodiment, the Z-direction is also considered by preparing plural inverse mapping mathematical expression models as described above.

As described above, the inverse mapping mathematical model in the scanning controller 10 is set to the 3-input and 3-output model. Therefore, the command values for the scanning electromagnet 3 and the kinetic energy command value for the charged particle beam 1 can be determined at a time, and the command values can be generated in consideration of the interference term effect between XY and Z, so that the beam position control can be implemented with higher precision.

Third Embodiment

FIG. 12 is a diagram showing the construction of a particle beam irradiation apparatus according to a third embodiment. 31 represents a final bending electromagnet provided to the beam transport system, and it is disposed upstream of the Y-direction scanning electromagnet 3b and deflects the charged particle beam to A, B and C passages. FIG. 6 of the first embodiment shows a simple case where the scanning electromagnet 3 is disposed at the most downstream side.

However, there is a case where the bending electromagnet is disposed at the downstream side of the scanning electromagnet (scanning electromagnet, wobbler electromagnet) or a case where the scanning electromagnet is omitted by making good use of the bending electromagnet. This invention can be applied to the above constructions. In these cases, the forward mapping from the command value coordinate space 6 to the beam irradiation position coordinate space 7 is more complicated, and thus the effect of this invention is greater.

In FIG. 12, the Y-direction scanning electromagnet 3b is used, and the final bending electromagnet 31 is brought with the function of the X-direction scanning electromagnet. The command value $I_a$ for the X-direction scanning electromagnet is generated from the final bending electromagnet 31, the charged particle beam is scanned, and the estimation value $I_{ae}$ of the command value for the X-direction scanning electromagnet is input to the final bending electromagnet 31. As described above, the final bending electromagnet 31 is brought with the same function as the X-direction scanning electromagnet.

Fourth Embodiment

FIG. 13 is a diagram showing the operation corresponding to a moving internal organ in a fourth embodiment. This invention does execution particularly when movement or deformation of an irradiation subject such as a tumor or the like which occurs in an internal organ moving due to breathing or the like is followed and treated on a real-time basis. This will be described with reference to FIG. 13. When a particle beam treatment is conducted by using the particle beam irradiation apparatus, it is necessary to first grasp the shape and position of a diseased site as an irradiation subject. Therefore, an image of the diseased site is three-dimensionally picked up by using an image pickup device such as CT, MRI, X-ray or the like. The particle beam treatment plan device plans out and supports creation of a treatment plan on the basis of the pickup three-dimensional video information (hereinafter referred to as a reference pickup image under treatment plan).

The particle beam irradiation apparatus executes particle beam irradiation on the basis of the treatment plan. Therefore, it has been hitherto necessary that a patient takes a posture on a patient holding device such as a bed or the like in a particle beam treatment room so that the posture concerned is as identical as possible to that when the patient is subjected to image pickup by image pickup device, and also a radiological technician executes a so-called "positioning work" of adjusting the movement of the patient holding device such as a bed or the like so that a pickup image is accurately coincident with the reference pickup image. For example, it is assumed that the lower right diagram of FIG. 13 represents an image pickup screen when a treatment is about to be conducted. In this case, this image pickup screen is different from a reference image pickup screen shown at the lower left diagram of FIG. 13, and thus it is necessary to adjust the movement of the patient holding device such as a bed or the like until both the image pickup screens are accurately coincident with each other.

Furthermore, there may occur a case where an internal organ moves due to breathing or the like and thus the shape of an irradiation subject (diseased site) is deformed (the upper right diagram of FIG. 13). For this problem, it has been hitherto required to take such a countermeasure that the breathing timing and the irradiation timing are matched with each other by using a breathing synchronizing device or the like. This positioning work and the breathing synchronizing work require the most time in the overall treatment, and thus it increases the treatment time per person and imposes a burden on the patient.

The particle beam irradiation apparatus according to the fourth embodiment of the present invention does not adopt a strategy of matching the position and posture of a diseased site under actual irradiation for a treatment with those of the reference pickup image under a treatment plan, but adopts a strategy of converting the desired irradiation coordinate on a real-time basis in conformity with the position and posture under actual irradiation for a treatment. As shown in FIG. 13, landmarks (feature sites or insertion markers) are determined in an irradiation subject in advance. The positions of the landmarks of the reference pickup image under the treatment plan are compared with the landmark positions of the pickup image under actual irradiation, whereby it is found how to convert the desired irradiation coordinates. Specifically, it is assumed that the reference pickup image of the irradiation subject (diseased site) under the treatment plan is converted to the image of the irradiation subject (diseased site) under actual irradiation by translational movement, rotational movement and enlargement/reduction (enlargement in some direction and reduction in another direction⇒deformation). That is, this is regarded as a kind of mapping, and it is assumed from the position variation information of the landmarks that all the points of the irradiation subject are moved by the same mapping.

The desired irradiation position coordinate under the treatment plan may be converted to the desired irradiation position coordinate under actual irradiation on the basis of the mapping concerned. The variation of the irradiation subject due to breathing occurs from moment to moment and thus it is necessary to execute the conversion of the desired irradiation coordinate on a real-time basis. The conventional method of generating the command values on the basis of the conversion table uses many IF sentences (conditional expressions for case classification), and thus it has been difficult for the method to generate the command value for the desired irradiation coordinate which varies from moment to moment.

When the command value generating method using the polynomial expressions shown in this invention is used, only addition and subtraction are used in the polynomial expressions. Therefore, this method can bring an effect that it is excellent in real-time processing, does not require the positioning work, is flexibly adaptable to even a case where an irradiation subject (diseased site) is moved or deformed due to breathing or the like, can shorten the treatment time and imposes no burden on patients, which has not been hitherto attained.

As described above, the desired irradiation position coordinate is corrected from the information of the irradiation subject under image pickup, and the scanning electromagnet is controlled on the basis of the command value generated from the corrected desired irradiation position coordinate by using the inverse mapping mathematical expression model to irradiate the charged particle beam onto the irradiation subject while scanning the charged particle beam. Therefore, the command value can be generated on a real-time basis. Furthermore, the desired irradiation position coordinate is corrected from the information of the irradiation subject under image pickup, and the scanning electromagnet and the kinetic energy of the charged particle beam are controlled on the basis of the command values generated from the corrected desired irradiation position coordinate by using the inverse mapping mathematical expression model, thereby irradiating the irradiating target while scanning the charged particle beam so that the command value can be generated on a real-time basis.

Fifth Embodiment

In the first embodiment and the second embodiment, the least square method is described as the method of determining the coefficients (unknown parameters) of the polynomial expression. When the coefficients (unknown parameters) of the polynomial expression are determined, a weighted least square method may be used. According to the weighted least square method, the calculation is performed while respective original data (actual data at the calibration time) for determining the coefficients (unknown parameters) of the polynomial expression are weighted. For example, there is a case where low-reliability data are obtained due to some factor (for example, electrical noise or the like) in the test irradiation for calibration. In this case, the low-reliability data are multiplied by a weight which is near to zero, whereby the influence of these data can be suppressed.

Furthermore, the irradiation subject may be divided into some areas, and the unknown parameters of the polynomial expression may be determined every area. In this case, when the polynomial expression of some area A is calculated, the calculation is performed while data belonging to the area A are multiplied by a weight "1" and data which do not belong to the area A is multiplied by a weight near to zero, whereby irradiation nearer to an actual phenomenon, that is, high-precision irradiation can be implemented.

The invention claimed is:

1. A particle beam irradiation apparatus comprising:
an accelerator;
a scanning electromagnet; and
a scanning controller for controlling the scanning electromagnet to irradiate a charged particle beam from the accelerator to an irradiation subject,
the scanning electromagnet having: an X-direction scanning electromagnet; and
a Y-direction scanning electromagnet for scanning in a direction perpendicular to a scanning direction of the X-direction scanning electromagnet,
the scanning controller having: an X-direction inverse mapping mathematical expression model for generating an X-direction command value for exciting the X-direction scanning electromagnet; and
a Y-direction inverse mapping mathematical expression model for generating a Y-direction command value for exciting the Y-direction scanning electromagnet,
from a desired irradiation position coordinate of the charged particle beam in the irradiation subject so that irradiation to the irradiation subject is implemented on the basis of the command values concerned,
each of the X-direction and Y-direction inverse mapping mathematical expression models containing all of two variables when the desired irradiation position coordinate on an irradiation position plane of the charged particle beam is represented by the two variables concerned,
wherein the X-direction and Y-direction scanning electromagnets are controlled on the basis of the X-direction and Y-direction command values generated from the desired irradiation position coordinate of the charged particle beam in the irradiation subject by the X-direction and Y-direction inverse mapping mathematical expression models, thereby irradiating the irradiation subject with the charged particle beam while scanning the charged particle beam.

2. The particle beam irradiation apparatus according to claim 1, wherein each of the X-direction and Y-direction inverse mapping mathematical expression models is a polynomial expression.

3. The particle beam irradiation apparatus according to claim 2, wherein the desired irradiation position coordinate is corrected from information on movement or deformation of the irradiation subject under image pickup, and the X-direction and Y-direction scanning electromagnets are controlled on the basis of the X-direction and Y-direction command values each generated from the corrected desired irradiation position coordinate by the X-direction and Y-direction inverse mapping mathematical expression models as polynomial expressions while following the movement or the deformation of the irradiation subject, thereby irradiating the irradiation subject with the charged particle beam while scanning the charged particle beam.

4. The particle beam irradiation apparatus according to claim 2, wherein unknown coefficients existing in each of the X-direction and Y-direction inverse mapping mathematical expression models as the polynomial expressions are determined by inputting plural pairs of command values preset for the X-direction and Y-direction scanning electromagnets to control the charged particle beam, and applying a least square method or a weighted least square method to actual data of actually irradiated irradiation position coordinates.

5. The particle beam irradiation apparatus according to claim 1, wherein plural pairs of X-direction and Y-direction inverse mapping mathematical models are provided, and the X-direction and Y-direction inverse mapping mathematical expression models to be used can be selected from the plural pairs of inverse mapping mathematical expression models.

6. The particle beam irradiation apparatus according to claim 1, wherein a bending electromagnet provided to a beam transport system is brought with a function of the X-direction or Y-direction scanning electromagnet.

7. A particle beam irradiation apparatus comprising:
an accelerator;
a scanning electromagnet; and
a controller for controlling the accelerator and the scanning electromagnet to irradiate a charged particle beam from the accelerator to an irradiation subject,
the scanning electromagnet having: an X-direction scanning electromagnet; and
a Y-direction scanning electromagnet for scanning in a direction perpendicular to a scanning direction of the X-direction scanning electromagnet,
the controller having: an X-direction inverse mapping mathematical expression model for generating an X-direction command value for exciting the X-direction scanning electromagnet; and
a Y-direction inverse mapping mathematical expression model for generating a Y-direction command value for exciting the Y-direction scanning electromagnet
from a desired irradiation position coordinate of the charged particle beam in the irradiation subject so that irradiation to the irradiation subject is implemented on the basis of the command values concerned,
each of the X-direction and Y-direction inverse mapping mathematical expression models being a polynomial expression containing all two variables when the desired irradiation position coordinate is represented by the two variables on an irradiation position plane of a charged particle beam, wherein unknown coefficients contained in the polynomial expressions are determined by inputting a plurality of pairs of preset X-direction and Y-direction command values to the X-direction and Y-direction scanning electromagnets to control a charged particle beam and performing a weighting least-square method of executing lower weighting on some data of actual data of irradiation position coordinates at which the charged particle beam is actually controlled and irradiated, thereby enhancing reliability.

8. A particle beam irradiation apparatus comprising:

an accelerator;

a scanning electromagnet; and a controller for controlling the accelerator and the scanning electromagnet to irradiate a charged particle beam from the accelerator to an irradiation subject, the scanning electromagnet having: an X-direction scanning electromagnet; and
- a Y-direction scanning electromagnet for scanning in a direction perpendicular to a scanning direction of the X-direction scanning electromagnet, the controller having: an X-direction inverse mapping mathematical expression model for generating an X-direction command value for exciting the X-direction scanning electromagnet; and a Y-direction inverse mapping mathematical expression model for generating a Y-direction command value for exciting the Y-direction scanning electromagnet from a desired irradiation position coordinate of the charged particle beam in the irradiation subject so that irradiation to the irradiation subject is implemented on the basis of the command values concerned, each of the X-direction and Y-direction inverse mapping mathematical expression models being a polynomial expression containing all two variables when the desired irradiation position coordinate is represented by the two variables on an irradiation position plane of a charged particle beam, wherein in order to determine unknown coefficients contained in the polynomial expression, the irradiation subject is divided into plural areas, and the unknown coefficients contained in the polynomial expression of each area are determined by inputting a plurality of pairs of preset X-direction and Y-direction command values to the X-direction and Y-direction scanning electromagnets to control a charged particle beam, and subjecting actual data of each actually-irradiated irradiation position coordinate to a weighting least-square method of executing weighting such that a weight of actual data belonging to the area concerned is larger than a weight of actual data which do not belong to the area concerned.

* * * * *